United States Patent [19]

Reszka et al.

[11] Patent Number: 6,090,955
[45] Date of Patent: Jul. 18, 2000

[54] LIPOSOME-ENCAPSULATED TAXOL, ITS PREPARATION AND ITS USE

[75] Inventors: Regine Reszka, Schwanebeck; Martin Brandl, Freiburg; Iduna Fichtner, Berlin; Gernot Warnke, Freiburg, all of Germany

[73] Assignee: Max-Delbrück-Centrum für Molekulare Medizin, Germany

[21] Appl. No.: 08/793,238

[22] PCT Filed: Aug. 18, 1995

[86] PCT No.: PCT/DE95/01163

§ 371 Date: Jun. 19, 1997

§ 102(e) Date: Jun. 19, 1997

[87] PCT Pub. No.: WO96/05821

PCT Pub. Date: Feb. 29, 1996

[30] Foreign Application Priority Data

Aug. 20, 1994 [DE] Germany .............................. 44 30 593

[51] Int. Cl.[7] ...................................................... C07D 493/00
[52] U.S. Cl. ............................................. 549/510; 514/449
[58] Field of Search .............................. 514/449; 549/510

*Primary Examiner*—Amelia Owens
*Attorney, Agent, or Firm*—Londa and Traub LLP

[57] ABSTRACT

The aim of the invention is to produce liposome-encapsulated taxol with a high taxol concentration and high stability and hence a high therapeutic effect. The invention involves the development of specific forms of taxol encapsulation and the use of these, optionally in combination with other substances, in the treatment of various types of tumor. The liposome-encapsulated taxol is characterized in that it is prepared by high-pressure homogenization or by aerosol formulation.

16 Claims, 1 Drawing Sheet

LIPOSOME-ENCAPSULATED TAXOL, ITS PREPARATION AND ITS USE

BACKGROUND OF THE INVENTION

This appln. is a 371 of PCT/DE95/01163 filed Aug. 18, 1995.

The invention relates to liposome-encapsulated taxol, its preparation and its use. Areas, in which the invention can be used, are medicine and the pharmaceutical industry.

Taxol is a natural product, which occurs in the bark of various species of yew (Taxaceae) and can be obtained from these barks (J. Amer. Chem. Soc., 93:2325 (1971)) or recently also by chemical synthesis (J. Amer. Chem. Soc., 1110:5917–5919 (1988)). Compared to previously known cytostatic drugs, taxol has a completely novel mode of action (Ann. N.Y. Acad. Sci. 466:733–744 (1986); Sartorelli, A. (ed.): Molecular Actions and Targets for Cancer Chemotherapeutic Agents. Academic Press, New York, 1981, pp. 483–507). The substance promotes the polymerization of microtubuli from tubuli dimers and stabilizes the microtubuli by inhibiting their depolymerization. Furthermore, there is an abnormal arrangement and bundling of microtubuli during the whole of the cell cycle, which leads to the formation of multiple, microtubular dividing stars during mitosis and, with that, to inhibition of the normal dynamic reorganization of the microtubular network. Since the vital cell function in the interphase and during mitosis are decisively affected thereby, taxol exhibits clear antineoplastic activity against different tumors, also implanted B16 melanoma and P388 leukemia and against human breast tumors.

The applicability of taxol is greatly limited by its low water solubility. Solubilizers, such as Cremophor (polyethoxylated castor oil) and alcohol improve the solubility but, when used, lead to appreciable side effects, such as anaphylactoid reactions. The dilution of such solutions with physiological salt solution for the administration has the disadvantage that the stability of taxol in physiological salt solution is inadequate (not more than 24 hours). A dose-limiting side effect is myelosuppression and, primarily, neutropenia (Semin. Oncol. 19:646–662 (1992). Because of their amphiphilic character, liposomes offer the possibility of encapsulating or incorporating water-soluble as well as lipid-soluble substances.

As a substance almost insoluble in water, taxol can be dissolved with high efficiency in the lipid phase of liposomes of suitable composition, so that the toxicities, due to Cremophor EL and observed in man, including an increased formation of chylomicrons, should no longer occur. The therapeutic effectiveness of free, liposome-encapsulated and nanoparticular taxol was compared in vitro on two leukemias, P388 and L1210. While the growth of P388 cells was inhibited equally by all three forms of the drug, L1210 exhibited a greater sensitivity towards the nanoparticular form.

When all 3 preparations were tested in vivo on P388 (12.5 mg/kg/4 days), the free and liposomal forms were comparable in their therapeutic effectiveness, while nanoparticular taxol caused acute toxicities (J. Microencapsul. 7 (2) 191–7 (1990)). In a further study, taxol was tested in the free and liposomal form with regard to the antitumor activity on two human glioblastoma in the nude mouse model (12.5 mg/kg/4 days). Both forms resulted in a significant decrease in tumor growth (in vivo 6 (1): 23–7, (1992)). Sharma et al. (Cancer Res. 53, 5877–81 (1993)) and Straubinger et al. (J. Natl. Cancer Inst. Monographs 15, 69–78 (1993)) reported that liposomal taxol (10–45 mg/kg) had a significant antitumor effect on the murine taxol-resistant colon-26 model. The encapsulation of taxol in liposomes and the use of the products obtained for the treatment of carcinoses is described in WO 93/18751. A combination of this treatment with hyperthermia is preferred. The taxol liposomes produced exhibit improved stability.

Previously, a patent application (WO 93/18751) was filed, in which a plurality of combinations of taxol and liposomes is claimed, of which, in particular, vesicles with a positive charge and based on cardiolipin, phosphatidyl choline and cholesterol were produced and investigated. However, the taxol, encapsulated in this manner, had to be administered on four consecutive days in the animal experiments, since a single administration evidently did not lead to the desired antitumor effect.

SUMMARY OF THE INVENTION

It is an object of the invention to make available liposome-encapsulated taxol, containing a high proportion of taxol and having a higher stability and, with that, a greater therapeutic effectiveness. In particular, the object of the invention is to develop specific forms of encapsulating taxol and to use these, optionally in combination with other free and/or liposome-encapsulated substances, for the treatment of different types of tumors and localizations. Aside from the possibility of a single administration of liposomal taxol, the prevention of the dose-limiting neutropenic effect of the not encapsulated taxol, for example, by a combination with liposomal carboplatinum, are in the foreground of endeavors.

Pursuant to the invention, the encapsulation is carried out by means of high-pressure homogenization and/or aerosol formation. Our own experiments include the work of preparing and characterizing different taxol-containing liposome types of different size and composition (see claims).

Yet another object of the invention is a pharmaceutical preparation, which contains the inventive, liposome-encapsulated taxol and conventional pharmaceutical carriers and additives. A mixture, which can be used advantageously in practice, contains 0.98 mg of taxol in 50 mg of phosphatidyl choline (98% of the amount of taxol used).

DETAILED DESCRIPTION OF THE INVENTION

Figure 1:
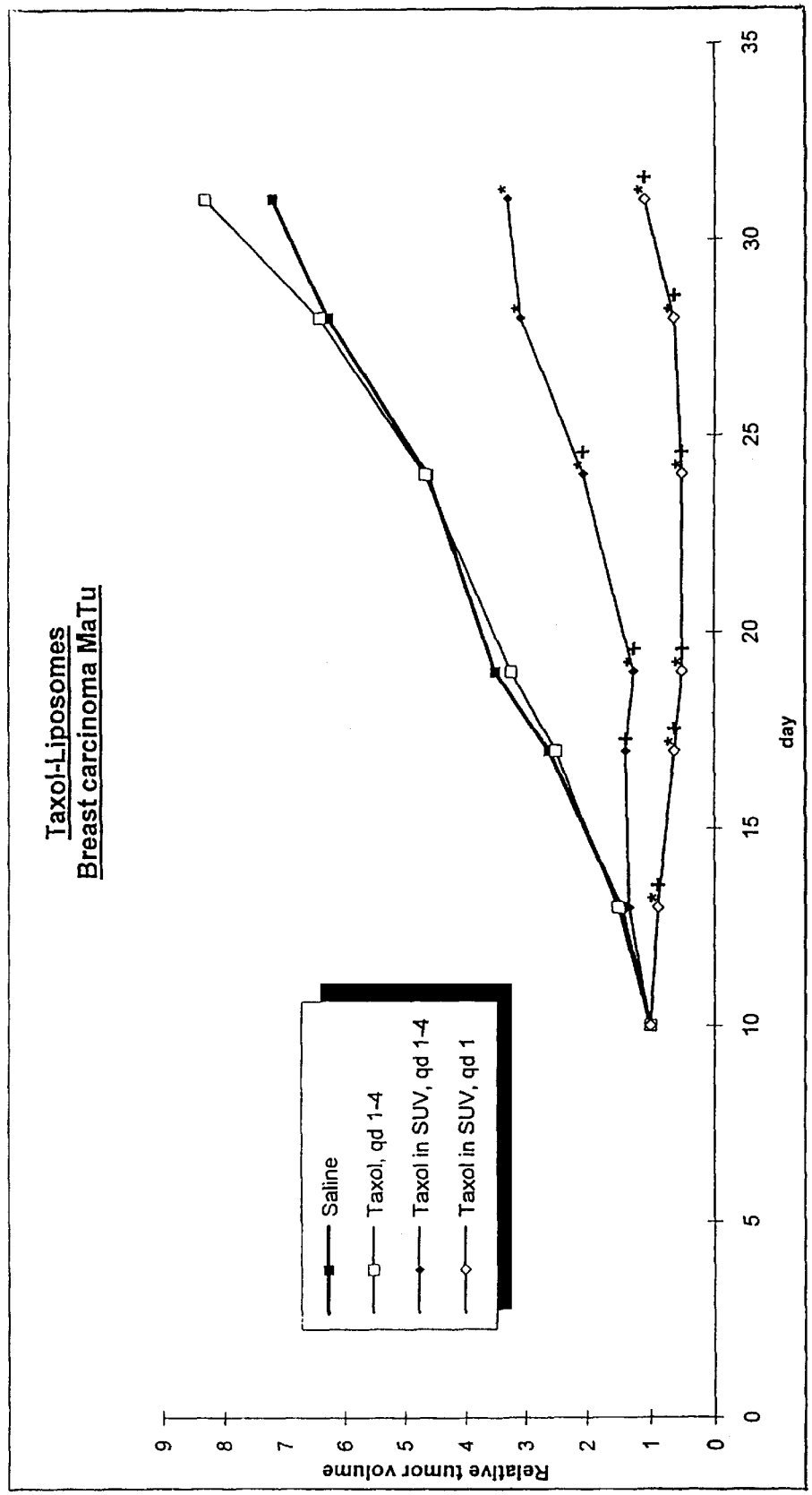
FIG. 1 shows a graph of relative tumor volume over time, with respect to several treatments.

The liposome encapsulation is accomplished by high-pressure homogenization or by spontaneous vesicle formation. In the first case, a previously produced liposome mixture in solid or liquid form is combined with taxol, subsequently homogenized repeatedly (preferably twice) at 5–160 MPa and then, if necessary, lyophilized.

The method for producing a taxol-containing liposomal preparation by means of high-pressure homogenization as well as, optionally, of releasing liposomes from such a preparation comprises the following steps:

1) Optional Preparation of a Lipid Film and Transferring the Film into a Pre-Mixture Consisting of Membrane-Forming Agents and an Aqueous Medium:

Premixture consisting of membrane-forming agents and aqueous medium: Preparation of a thin, dry lipid film by dissolving the taxol together with the membrane-forming agents in organic solvents. Subsequently, complete removal of the solvent by evaporation, optionally by spray drying. Dispersing the lipid film after addition of the aqueous medium, for example, by shaking, stirring, kneading, etc., optionally at an elevated temperature (approximately 10° C. above the phase transition temperature of the phospholipids).

2) High-Pressure Homogenization:

Either the pre-mixture obtained from 1 or, alternatively, a mixture of lipid(s), water and taxol (optionally dispersed coarsely by stirring, for example, by means of a magnetic stirrer, etc.) is subjected once or several times (however, not more than fifty times) to high-pressure homogenization (for example, by means of an APV Gaulin Micron Lab) at pressure between 5 and 160 Mpa (50 to 1600 bar). Educt, homogenizer and product optionally are tempered.

3) Optional Freeze-Thaw Treatment

By thawing and freezing the preparation once or several times during, that is, between individual cycles of the high-pressure homogenization or at the end of such cycles, a more homogeneous mixing of the formulation is achieved and the pre-formed liposomes possibly are temporarily destabilized, so that liposomes are formed, in which even more taxol is incorporated.

4) Optional Freeze-Drying and Redispersing

By freeze-drying one or more times and subsequently redispersing the preparations preferably during, that is, between individual cycles of the high-pressure homogenization or at the end of such cycles, a homogeneous mixture of the formulation is achieved and the pre-formed liposomes are temporarily destabilized, so that liposomes with even more incorporated taxol are formed.

5) Optional Conversion of the Preparation into a Free-Flowing Liposome Dispersion:

By the stepwise addition of aqueous medium, in an amount of 1 to 30% by volume of the preparation and mixing mechanically, for example, by manually shaking or by means of a vortex mixer, the three-dimensional gel structure is destroyed and the pre-formed liposomes are released.

6) Optional Filtration of the Liposome Dispersion

In the event that the size of the liposome is to be kept below an upper limit or a sterile preparation is to be obtained, the liposome dispersion can be filtered through filters with a pore width of 0.1 µm to 1 µm.

The inventive preparation, which contains tightly packed liposomes (liposome gel), is suitable as an active ingredient depot, which releases the active ingredient slowly and, moreover, either in dissolved form or in the form of individual, active ingredient-containing liposomes. This preparation can be administered by injection (for example, by i.m. or i.p. injection) or by implantation. However, an introduction into body cavities or an administration onto mucous membranes, onto the cornea of the eye or on sections of skin is also possible. Accordingly, the preparation serves as a carrier of the active ingredient as well as for the modified release of the latter.

The inventive preparation, which contains liposomes in free-flowing form, is suitable as a carrier of the active ingredient. This preparation can be administered by injection (for example, by i.v. or i.m. injection) or also by introduction into body cavities or application on mucous membranes, on the cornea of the eye or on sections of the skin. The inventive, encapsulated liposomes lead to a distribution of the active liposomal ingredients in the body, which selectively brings about a high and long lasting concentration of active ingredient at the site of action and with that, an improvement in the effect or an improvement in the ratio of effect to side effects.

For spontaneous vesicle formation, the taxol / encapsulating agent / blowing gas mixture is sprayed from metering aerosols and, after evaporation of the blowing gas, spontaneously forms liposome-encapsulated taxol on the lung surface. Alternatively, preformed taxol liposomes can be atomized. This procedure is to be preferred especially when direct use against lung metastases is intended.

The liposome-encapsulated taxol can be used as a cytostatic agent either by itself or in combination with other active ingredients, such as carboplatinum or liposome-encapsulated carboplatinum. Preferred is the use against brain tumors, malignant melanoma, liver metastases, lung metastases, breast cancers and urogenital cancers. The treatment of, for example, a human breast carcinoma on the nude mouse resulted, after a single administration of 50 mg/kg of liposome-encapsulated taxol, in a significant inhibition of tumor volume in comparison to a group treated with taxol (4×12.5 mg/kg).

The invention will be described in greater detail in the following by means of examples.

EXAMPLE 1

A lipid film, consisting of 1,500 mg of egg phosphatidyl choline and 30 mg of taxol is dispersed in 30 mL of sterile, calcium-free phosphate-buffered (pH 7.2–7.4) salt solution. The resulting dispersion of multilayered liposomes is treated in the high-pressure homogenizer (Gaulin Mikrolab 40) at 700 bar. The resulting liposome dispersion (SUV) can be stored briefly at 4° C. and is suitable for parenteral (i.v.) administration. Gel formation or lyophilization is suitable for longer storage.

EXAMPLE 2

Liposomes, prepared as in Example 1, are atomized with a suitable atomizer (such as Aero-Tech II) and thus made accessible for inhalative administration.

EXAMPLE 3

Taxol (200 mg), 200 mg of encapsulating agent of claim 2 and 400 $\mu$L of ethanol (90%) are added to a gas cylinder. After flanging on a metering valve (such as Perfect Valois DF 10/150 ACT), the preparation is mixed with 10 mL of pressure-liquefied dimethyl ether, so that a clear to opalescent or slightly cloudy solution results.

EXAMPLE 4

Like Example 3, however, a pressure liquefied isobutane is used as blowing gas.

EXAMPLE 5

Like Example 3, however, a pressure liquefied propane/butane (15/85) is used as blowing gas.

Liposomes of Example 1 were used for the animal experiments. It was possible to show, for example, on a human breast cancer (MaTu) that this liposome preparation, already after a single administration of 50 mg/kg, exhibited a better therapeutic effectiveness and a lower hemotoxicity than did free taxol (4 days treatment, 12.5 kg/mg per day) (Table 1 and FIG. 1).

TABLE 1

Breast Cancer MaTu

| | | Animals:<br>Tumor:<br>Therapy: | | Ncr:nu/nu<br>MaTu<br>i.p. | | female<br>s.c. | |
|---|---|---|---|---|---|---|---|
| Group | Nude mice | Substance | Treatment (d) | Dose (mg/kg/inj.) | Toxic deaths (d) | BWC (%) d10-13 | Tumor growth |
| A | 8 | Saline | 10–13 | | | 1 | see Figure |
| B | 8 | Taxol | 10–13 | 12.5 | 1(16) | −1 | |
| C | 8 | Taxol in SUV J918 | 10–13 | 12.5 | 2(21,32) | 1 | |
| D | 8 | Taxol in SUV | 10 | 50 | | | |

Comments:
Liposomes are better than free taxol
Single treatment = treatment on 4 consecutive days (depot effect?)
Same body weight in all groups The following are used as encapsulating agent a) a natural, semi-synthetic or fully synthetic amphiphilic material, such as a lipid, a surfactant or an emulsifier, b) a charged lipid component and/or a saturated lipid component and/or an ether lipid component c) a polymer d) a carrier liquid and, optionally, inactive materials, such as nanoparticles contains.

The amphiphilic material preferably has the formula given in claim 3. As charged lipid component, the anion of dicetyl phosphate, of palmitic acid, of stearic acid, the anion of a phospholipid, such as phosphatidyl serine, phosphatide acid or the anion of a sphingolipid, such as sulfatide are preferably used. In a particularly advantageous embodiment of the invention, phosphatidyl glycerol is used as charged lipid component.

The invention can be realized equally well with neutral lipid components, such as phosphatidyl choline, or saturated lipid components, such as dipalmitoyl phosphatidyl choline. As polymer, for example a polyethylene glycol with a molecular weight of 2,000–10,000 is used and, as carrier liquid, generally is physiological salt solution.

We claim:

1. A liposome-encapsulated taxol.

2. The liposome-encapsulated taxol of claim 1, comprising as encapsulating agent a) a natural, semi-synthetic or fully synthetic amphiphilic material, b) one or more of a charged lipid component, a saturated lipid component and an ether lipid component c) a polymer and d) a carrier liquid.

3. The liposome-encapsulated taxol of claim 1, wherein it contains a natural, semi-synthetic or fully synthetic amphiphilic compound of formula

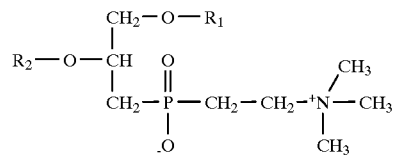

wherein $R_1$ and $R_2$ represent $C_{10}$ to $C_{20}$ alkanoyl, alkenoyl, alkyl or alkenyl.

4. The liposome-encapsulated taxol of claim 1, wherein, as charged lipid component, it contains one chosen from the group consisting of the anion of dicetyl phosphate, palmitic acid, stearic acid, the anion of a phospholipid, phosphatide acid, and the anion of a sphingolipid.

5. The liposome-encapsulated taxol of claim 1, wherein it contains, as charged lipid components, a chemically modified phosphatidyl ethanolamine, over which proteins can be coupled.

6. The liposome-encapsulated taxol of claim 1, wherein it contains phosphatidyl choline as neutral lipid components.

7. The liposome-encapsulated taxol of claim 1, wherein it contains phosphatidyl serine as charged lipid components.

8. The liposome-encapsulated taxol of claim 1, wherein it contains phosphatidyl glycerol as charged lipid components.

9. The liposome-encapsulated taxol of claim 1, wherein it contains dipalmitoyl phosphatidyl choline as saturated lipid components.

10. The liposome-encapsulated taxol of claim 1, wherein it contains dimyrestoyl phosphatidyl choline as saturated lipid components.

11. The liposome-encapsulated taxol of claim 1, wherein it contains ether lipids as charged lipid components.

12. The liposome-encapsulated taxol of claim 1, wherein it contains polyethylene glycol in or at the membrane of the vesicle.

13. A pharmaceutical preparation containing an effective amount of encapsulated taxol of claims 1 and pharmaceutically conventional carriers and additives.

14. A method for the preparation of liposome-encapsulated taxol of claim 1, wherein a mixture of membrane-forming amphiphiles, in which taxol was dissolved, and an aqueous phase, followed by removal of the solvent by evaporation and dispersal in water, is subjected one or more times but not more than fifty times to a high-pressure homogenization at pressures of 50 to 1,600 bar.

15. A method for producing liposome-encapsulated taxol by aerosol formation, wherein a previously produced liposome mixture in solid or liquid form is combined with taxol and subsequently treated in special aerosol forming equipment.

16. A method for producing liposome-encapsulated taxol, wherein taxol and the encapsulating agent are present in dissolved form in a pressure-liquefied blowing gas and, after evaporation of the blowing gas, are converted to encapsulated taxol by spontaneous vesicle formation on the epithelium of the lungs.

* * * * *